United States Patent [19]

Pilgram

[11] 4,358,611

[45] Nov. 9, 1982

[54] PREPARATION OF 2-PHENYLSEMICARBAZIDES

[75] Inventor: Kurt H. G. Pilgram, Modesto, Calif.

[73] Assignee: Shell Oil Company, Houston, Tex.

[21] Appl. No.: 867,750

[22] Filed: Jan. 9, 1978

[51] Int. Cl.$^3$ .................. A01N 9/20; C07C 133/02
[52] U.S. Cl. ........................................ 564/34; 71/120
[58] Field of Search ............... 260/554, 566 B, 691; 71/120; 564/34

[56] References Cited

U.S. PATENT DOCUMENTS

| 3,171,857 | 3/1965 | Benzing | 260/554 |
| 3,280,187 | 10/1966 | Meyer et al. | 260/554 |
| 3,576,864 | 4/1971 | Nagarajan | 260/554 |
| 3,755,443 | 8/1973 | Sheppard et al. | 260/554 |
| 3,984,463 | 10/1976 | Pilgram | 260/554 |
| 4,050,918 | 9/1977 | Pilgram | 71/120 X |
| 4,099,956 | 7/1978 | Pilgram | 71/120 |

FOREIGN PATENT DOCUMENTS 2342688  3/1974  Fed. Rep. of Germany.

OTHER PUBLICATIONS

Crekov et al. Chem. Abs. vol. 73, 1970, 109 134(e) "Structure & Reactivity of Hydrazine Derivatives, etc.".

Karady et al., Chem. Abs. vol. 78, 1973, 97,227(a) "Synthesis of α- Acrylarahydrazines".

*Primary Examiner*—Thomas A. Waltz

[57] ABSTRACT

2-Phenylsemicarbazides are prepared by a multi-step process involving:

(a) treating a phenylhydrazine, or salt thereof, with a chloroformate;
(b) adding phosgene;
(c) treating the resulting product with an amine; and
(d) hydrolyzing the resulting acylated semicarbazide.

The reaction can proceed through a $\Delta^2$-1,3,4-oxadiazolin-5-one intermediate formed with heating in step (b). Certain of the products are novel compounds.

15 Claims, No Drawings

PREPARATION OF 2-PHENYLSEMICARBAZIDES

BACKGROUND OF THE INVENTION

1. Field of the Invention

This invention relates to a new method for preparation of 2-phenylsemicarbazides.

2. Description of the Prior Art

There are relatively few examples in the prior art of groups useful for protecting the $NH_2$ group of a (substituted)phenylhydrazine while a carbamoylation is carried out on the remaining NH group adjacent to the (substituted)phenyl. In all the known examples, the $NH_2$ group is protected by converting the phenylhydrazine into the corresponding benzaldehyde phenylhydrazone prior to carbamoylation. Historically the benzaldehyde protective group has been removed by addition of equimolar amounts of 2,4-dinitrophenylhydrazine or more recently by refluxing in dilute aqueous hydrochloric acid and removing benzaldehyde azeotropically with steam as it is formed. Applicant has now discovered an alternate synthesis that avoids the use and recovery of benzaldehyde, a relatively expensive and toxic intermediate protective group.

No prior art has been found by applicant which describes the new multi-step process of the present invention.

U.S. Pat. Nos. 3,585,200 and 3,755,443 disclose the reaction of certain 2-substituted-$\Delta^2$-1,3,4-oxadiazolin-5-ones with alkylene diamines to form 4,4'-alkylene bis(1-acylsemicarbazides), which may then be hydrolyzed to the diacid salts by heating with aqueous mineral acids to produce materials suitable for use as blowing agents in polymers.

SUMMARY OF THE INVENTION

The process of the present invention is directed to the preparation of 2-phenylsemicarbazides unsubstituted at the 1-position, which comprises the steps of (a) treating a phenylhydrazine, or salt thereof, with a chloroformate;

(b) adding phosgene;

(c) treating the resulting product of (b) with an amine; and (d) hydrolyzing an acylated semicarbazide from (c).

Certain of the products are novel compounds.

DETAILED DESCRIPTION OF THE INVENTION

The process of the invention is readily applicable to the preparation of any 2-phenylsemicarbazides in which the nitrogen atom in the 1-position is devoid of substitutions other than by two hydrogen atoms:

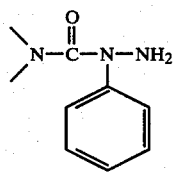

Examples of such semicarbazides are described in German patent publications 2,342,688 and 2,519,393 and in U.S. Pat. No. 3,984,463. The process is particularly useful when used for the preparation of 2-phenylsemicarbazides of the formula

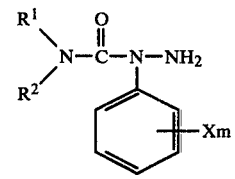

wherein $R^1$ and $R^2$ each independently represents hydrogen, lower alkyl of 1 to 6 carbon atoms or when taken together an alkylene group of 4 or 5 carbon atoms optionally interrupted by one or more oxygen atoms; X represents $NO_2$, a halogen atom of atomic number from 9 to 35, inclusive, amino or mono- or dialkylamino, or a group $-Y_p$-alkyl in which Y represents oxygen, or sulfur, p is 0 or 1 and in which the alkyl portion contains from 1 to 4 carbon atoms optionally substituted by one or more halogen atoms of atomic number from 9 to 35, inclusive, and m is 0 or an integer of from 1 to 5, preferably 0, 1 or 2. Compounds where substituents are located at the 3 and/or 4-position of the phenyl ring are among the most herbicidally active products of the process.

In step (a) the reactant chloroformate is either an alkyl or aryl chloroformate, preferably a lower alkyl chloroformate in which the alkyl group contains from 1 to 4 carbon atoms such as ethyl chloroformate, or phenyl chloroformate. The reaction with the phenylhydrazine is conducted in the presence of a tertiary-amine. A variety of alkyl, aryl and heterocyclic tert-amines can be used, e.g., pyridine, picoline, dimethylaniline and the like, but because of their ready availability lower alkyl tert-amines in which the alkyl groups each contain 1 to 6 carbon atoms are preferred such as trimethylamine, triethylamine and especially ethyldiisopropylamine. About one molar equivalent of amine is normally used but when the phenylhydrazine salt is used then two molar equivalents of amine should be employed.

It is preferred to add the chloroformate slowly, e.g., dropwise, while agitating, e.g., stirring and cooling the solution of phenylhydrazine and tert-amine. Solvents suitable for use in this step are numerous: any material in which the hydrazine is soluble but not containing a carbonyl or hydroxy group (ketone, aldehyde or alcohol). Examples of suitable classes of solvents include chlorinated hydrocarbons such as chloroform, carbon tetrachloride and the like, hydrocarbons including benzene, toluene, xylene, hexane and the like or mixtures of hydrocarbons, nitriles such as acetonitrile, esters such as ethyl acetate and ethers such as diethyl ether, tetrahydrofuran and the like. Tetrahydrofuran, diethyl ether, toluene and xylene are preferred. The reaction is conducted at temperatures ranging from ambient to the refluxing temperature of the solvent employed. Generally, the temperature is between 0°–25° C. when the chloroformate is being added, preferably 0°–5° C. But the resulting reaction may be sufficiently exothermic that the reaction mixture is cooled, e.g., with ice. The carbazate product may be used directly in reaction (b) although it is preferable to at least remove the amine salt, e.g., by filtering.

In step (b) the process with phosgene conveniently proceeds at ambient temperatures, e.g., 0°–40° C. This reaction step does not require a base-acceptor. The use of a solvent is preferred and conveniently the same one used in reaction (a). Ethyl acetate, tetrahydrofuran, benzene, toluene and xylene are particularly useful solvents in this step.

The chloroformyl products of this step are stable compounds which can be isolated in high yields under anhydrous conditions. However, for convenience one may proceed directly to step (c) without isolating the products of step (b).

In step (c) the process proceeds rapidly at ambient temperatures, 0°-40° C., upon addition of the secondary amine reactant. Slight cooling may be useful during the addition. Any secondary amine may be used, including alkyl, aryl or heterocyclic secondary amines such as piperidine, morpholine, N-methylaniline as appropriate to produce the desired product, e.g., as defined by $R^1$ and $R^2$ in formula I. The preferred herbicidally active compounds are generally prepared from dialkylamines in which the alkyl groups each contain from 1 to 6 carbon atoms. Dimethylamine and diethylamine react readily. At least 3 molar equivalents of secondary amine per mole of 2-(chlorocarbonyl)-2-(phenyl)hydrazinecarboxylic acid ester are generally required in order to neutralize hydrogen chloride by-product as well as to participate in the reaction with 2-(chlorocarbonyl)-2-(phenyl)hydrazinecarboxylic acid ester. The reaction is preferably conducted in the presence of a solvent which is again the same solvent in the preceding reaction (b).

Under acidic conditions, the reaction products are hydrolytically stable. However, under alkaline conditions the products readily hydrolyze to give 2-phenylsemicarbazides. This is step (d) in the process of the invention.

In step (d) of the process any alkaline material may be used to effect hydrolysis but inorganic compounds are very convenient and in particular alkali metal hydroxides such as sodium hydroxide or potassium hydroxide. The alkaline material is added in the amounts of 1 to 4 moles in excess of that required. The reaction takes place in an aqueous medium and optionally an organic solvent. The organic solvent can be a lower alcohol of 1 to 4 carbon atoms, e.g., ethanol. A solution of 25-40% aqueous ethanol, ideally 35% is useful.

The hydrolysis proceeds best when the reaction mixture is heated, preferably to reflux (about 80°-90° C.) for 1-10 hours depending on the specific reactant.

The 2-phenylsemicarbazide final product is readily recovered and purified by conventional recovery procedures known in the art. For example the product is acidified by addition of a mineral acid such as HCl or the like. Then the product is made slightly basic by adding, e.g., alkali metal hydroxide, to precipitate the product 2-phenylsemicarbazide which is isolated, e.g., by extraction or filtration or crystallization.

The overall process of the invention is particularly useful in the preparation of 2-phenylsemicarbazide due to the low cost of reagents used, the mild reaction conditions, the rapid reaction times, the apparent absence of side reactions and the resulting high yield and purity of products produced.

A variation in the process of the invention can be made in step (b) by heating the reaction mixture to reflux until a 2-ethoxy-4-phenyl-$\Delta^2$-1,3,4-oxadiazoline-5-one is formed and no more hydrogen chloride gas is evolved. When this is done and the product is used in step (c), only 1 mole equivalent of secondary amine reactant is necessary. Otherwise the reaction conditions for step (c) when using a 2-ethoxy-4-phenyl-$\Delta^2$-1,3,4-oxadiazolin-5-one are as previously described above with regard to step (c).

Another aspect of the invention is based upon the fact that a larger variety of 4-phenyl-2-substituted-$\Delta^2$-1,3,4-oxadiazolin-5-ones can be used to react with secondary amines to produce 2-phenylsemicarbazides. Thus any oxadiazolinone of the formula

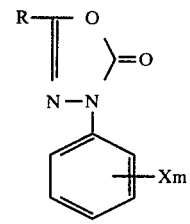

wherein X and m are as previously defined and R is alkyl, cycloalkyl, alkenyl, or alkoxy group of up to 10 carbon atoms, $CF_3$ or an aryl, aralkyl, or aryloxy group containing 6 to 10 carbon atoms.

Other methods are available to prepare these oxadiazolinones. For example, one involves the reaction of a 2-phenylsemicarbazide

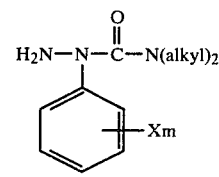

with an acid anhydride particularly a lower acyclic acid anhydride such as pivalic anhydride. The reaction is conveniently conducted in the absence of added solvent and at elevated temperatures of between about 50°-170° C. This is useful when a 2-phenylsemicarbazide containing different substituents at the 4-position is desired.

Another method of preparing the oxadiazolinones is disclosed in U.S. Pat. No. 3,846,440 and involves the reaction of a 2-substituted-$\Delta^2$-1,3,4-oxadiazolin-5-one with a halogenonitrobenzene as follows:

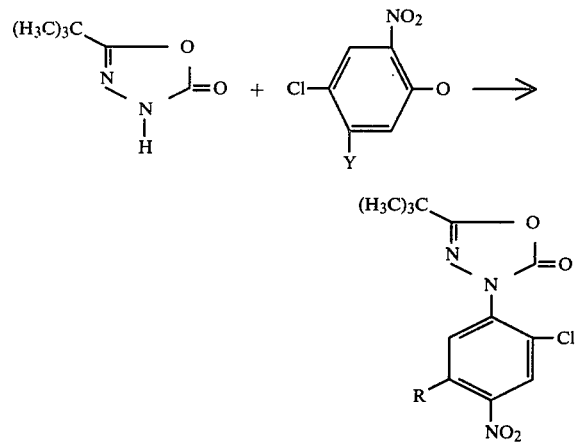

in which the $NO_2$ group of the product is subsequently reduced, the resulting amino group diazotized and the diazonium group replaced by chlorine.

Examples of compounds which can be prepared using the process of the present invention include:

4,4-dimethyl-2-(3,4-dichlorophenyl)semicarbazide,
4,4-dimethyl-2-(3-(trifluoromethyl)phenyl)semicarbazide,
4,4-dimethyl-2-(3-(trifluoromethoxy)phenyl)semicarbazide,
4,4-dimethyl-2-(2,4-dichlorophenyl)semicarbazide,
4,4-dimethyl-2-(3-chloro-4-fluorophenyl)semicarbazide,
4,4-dimethyl-2-(3,4-difluorophenyl)semicarbazide,
4,4-dimethyl-2-(3-trifluoromethyl)-4-fluorophenyl)-semicarbazide,
4,4-dimethyl-2-(3-(trifluoromethyl)-4-chlorophenyl)-semicarbazide,
4,4-dimethyl-2-phenylsemicarbazide,
4,4-dimethyl-2-(3-(trifluoromethyl)-4-isopropoxyphenyl)semicarbazide,
4,4-dimethyl-2-(2,3,4,5,6-pentafluorophenyl)semicarbazide,
4,4-dimethyl-2-(3-(trifluoromethyl)-4-methoxyphenyl)semicarbazide,
4,4-dimethyl-2-(3-chloro-4-isopropoxyphenyl)semicarbazide,
4,4-dimethyl-2-(3-chloro-4-(isopropylthio)phenyl)-semicarbazide,
4,4-dimethyl-2-(3-chloro-4-methoxyphenyl)semicarbazide,
4,4-dimethyl-2-(3-chloro-4-(methylthio)phenyl)-semicarbazide,
4,4-dimethyl-2-(3-(trifluoromethyl)-4-(p-chlorophenoxy)phenyl)semicarbazide,
4,4-dimethyl-2-(4-chlorophenyl)semicarbazide,
4,4-diethyl-2-(3,4-dichlorophenyl)semicarbazide,
4,4-diethyl-2-phenylsemicarbazide,
4,4-dimethyl-2-(4-bromophenyl)semicarbazide,
4,4-dimethyl-2-(4-(p-chlorophenoxy)phenyl)semicarbazide,
4-morpholinecarboxylic acid 1-phenylhydrazide,
2-(3,4-dichlorophenyl)semicarbazide,
4,4-dibutyl-2-(3-chloro-4-fluorophenyl)semicarbazide,
4,4-dipropyl-2-(3-chloro-4-isopropoxyphenyl)semicarbazide,
4,4-dibutyl-2-(3,4-dichlorophenyl)semicarbazide,
4-methyl-4-butyl-2-(3-(trifluoromethyl)phenyl)semicarbazide,
4-ethyl-4-propyl-2-(4-bromophenyl)semicarbazide,
4-methyl-4-hexyl-2-(3,4-difluorophenyl)semicarbazide,
4,4-dimethyl-2-(3(chlorodifluoromethylthio)phenyl)semicarbazide,
4,4-dimethyl-2-(2,4-dichloro-5-isopropoxyphenyl)-semicarbazide,
4,4-dimethyl-2-(4-bromo-3-tolyl)semicarbazide,
4,4-dimethyl-2-(3-chloro-4-bromophenyl)semicarbazide, 2-Phenylsemicarbazides of the present invention are useful as herbicides, either as selective herbicides or broad spectrum herbicides, depending on the species. The broad class of compounds and their use as herbicides are described in German patents 2,342,688 and 2,519,393, and in U.S. Pat. No. 3,984,463.

Illustrative Embodiments

The process of the present invention is illustrated in the following examples which demonstrate the preparation of typical species. In the examples, the identities of the compounds, both intermediates and final, were confirmed by elemental analysis and infrared and nuclear magnetic spectral analysis. The examples are for the purpose of illustration only and should not be regarded as limiting the invention in any way.

Embodiment I 4,4-Dimethyl-2-(3-chloro-4-fluorophenyl)semicarbazide

A mixture of 144.9 g of 3-chloro-4-fluoroaniline and 705 ml of concentrated hydrochloric acid was stirred and heated to 80° C. The mixture containing the aniline hydrochloride was allowed to cool to ambient temperature. After 24 hours, the mixture was stirred and cooled to 5°–10° C. while a solution of 69.5 g of sodium nitrite in 350 ml of water was added dropwise within ½ hour. After an additional ½ hour, the solution containing the diazonium salt was gradually added with stirring to a solution of 427 g of stannous chloride ($2H_2O$) in 700 ml of hydrochloric acid. After 45 minutes at ambient temperature, the reaction mixture was made alkaline by the addition of 3000 ml of 50% sodium hydroxide and extracted with ether. The combined ether extracts were dried ($MgSO_4$), filtered and concentrated to give 214.1 g (67%) of 3-chloro-4-fluorophenylhydrazine as a tan solid; melting point 75°–77° C.

To a stirred solution containing 50.0 g of the above hydrazine and 14.8 g of triethylamine in 500 ml of tetrahydrofuran was added 37.2 g of ethyl chloroformate. After ½ hour, the reaction mixture was suction filtered and the solid was washed with tetrahydrofuran. The filtrate was concentrated to dryness, dissolved in ether and washed well with water. Concentration of the dried solution and crystallization of the residue from ether-hexane gave 30.7 g (42%) of hydrazinecarboxylic acid, 2-(3-chloro-4-fluorophenyl)-, ethyl ester as a tan crystalline solid; melting point 99°–100° C.

To a stirred solution containing 9.5 g of the above hydrazine-carboxylic acid ester in 150 ml of ethyl acetate was added 4.5 g of phosgene through a gas-inlet tube. Analysis after ½ hour indicated conversion to hydrazinecarboxylic acid, 2-(chlorocarbonyl)-2-(3-chloro-4-fluorophenyl)-, ethyl ester. After evaporative removal of excess phosgene and about 50 ml of ethyl acetate, the residual solution was treated with 2.0 g of dimethylamine. After 1 hour, the reaction mixture was concentrated to dryness and the product was purified by silica chromatography to give 5.5 g (44%) of hydrazinecarboxylic acid, 2-((dimethylamino)carbonyl)-2-(3-chloro-4-fluorophenyl)-, ethyl ester as a white crystalline solid; melting point 69°–73° C.

A solution of 10.7 g of the above ester and 7.0 g of sodium hydroxide in 100 ml of ethanol and 150 ml of water was refluxed at 83° C. for 3.5 hours. The reaction mixture was concentrated to a volume of about 150 ml, acidified with hydrochloric acid, then made alkaline to a pH of 8.5 with sodium hydroxide and extracted with ether. The combined ether extracts were dried ($MgSO_4$), and concentrated, and the residue was recrystallized from ether-hexane to give 7.1 g (88%) of 4,4-dimethyl-2-(3-chloro-4-fluorophenyl)semicarbazide as a white crystalline solid; melting point 88°–89° C.

Embodiment II

Following the process method similar to Embodiment I and substituting phenyl chloroformate for ethyl chloroformate in the first reaction, 4,4-dimethyl-2-(3-chloro-4p-fluorophenyl)semicarbazide was prepared in 44% yield.

Embodiment III

4,4-Dimethyl-2-(4-chlorophenyl)semicarbazide

A solution of 21.5 g of 4-chlorophenylhydrazine hydrochloride and 113.5 g of ethyldiisopropylamine in 300 ml of tetrahydrofuran was cooled to −10° C. and stirred during the dropwise addition of 47.7 g of ethyl chloroformate. The reaction mixture was stirred at ambient temperature for 1 hour, then filtered, and the solid was washed with ether. The filtrate was washed with water, dried (MgSO$_4$), and concentrated. Recrystallization from hexane-ether gave 73.3 g (81%) of hydrazinecarboxylic acid, 2-(4-chlorophenyl)-, ethyl ester as a white crystalline solid; melting point 89°–92° C.

To 35.9 g of the above hydrazinecarboxylic acid ethyl ester in 150 ml of ethyl acetate at 5° C. was added 18.2 g of phosgene. After 45 minutes at ambient temperature, the solvent was removed under reduced pressure. Recrystallization of the residual oil from hexane-ether gave 41.0 g (89%) of hydrazinecarboxylic acid, 2-(chlorocarbonyl)-2-(4-chlorophenyl)-, ethyl ester as a white crystalline solid; melting point 70°–75° C.

Preferably instead of isolating the above hydrazinecarboxylic acid ethyl ester, a similar product mixture was concentrated to a volume of about 100 ml and treated with 8.3 g of dimethylamine. The resulting reaction mixture was washed with water, dried (MgSO$_4$) and concentrated. Crystallization from ether-hexane gave 41.6 g (87%) of hydrazinecarboxylic acid, 2-((dimethylamino)carbonyl)-2-(4chlorophenyl)-, ethyl ester as a white crystalline solid; melting point 63°–66° C.

A solution containing 20.0 g of the above hydrazinecarboxylic acid ethyl ester and 14.0 g of sodium hydroxide in 250 ml of water and 175 ml of ethanol was refluxed at 83° C. for 3 hours and concentrated to a volume of 175 ml. The cooled reaction mixture was acidified with hydrochloric acid and then made alkaline to a pH of 8 by addition of dilute sodium hydroxide. Extraction with ether of the basic solution gave 12.5 g (84%) of 4,4-dimethyl-2-(4-chlorophenyl)semicarbazide as a viscous oil.

Embodiment IV

Following a procedure similar to that of Embodiment III above, 4,4-dimethyl-2-(4-bromophenyl)semicarbazide was prepared in 35% yield; melting point 65°–66° C.

Embodiments V-X

Following process methods similar to those used in Embodiments I and III, the following 2-phenylsemicarbazides were prepared as shown in Table I.

TABLE I

2-Phenylsemicarbazides

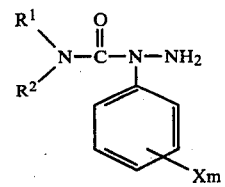

| Embodiment | R$^1$ | R$^2$ | Xm | % Yield | M.P., °C. |
|---|---|---|---|---|---|
| V | CH$_3$ | CH$_3$ | H | 77 | Oil |
| VI | C$_2$H$_5$ | C$_2$H$_5$ | H | 78 | Oil |
| VII | CH$_3$ | CH$_3$ | 3,4-Cl$_2$ | 70 | 72–74 |
| VIII | C$_2$H$_5$ | C$_2$H$_5$ | 3,4-Cl$_2$ | 97 | 59–62 |
| IX | —CH$_2$(CH$_2$)$_3$CH$_2$— | | 3,4-Cl$_2$ | 54 | 105–108 |
| X | CH$_3$ | CH$_3$ | 4-(p-chlorophenoxy) | 17 | viscous oil |

In like manner, 4,4-dimethyl-2-(3-(trifluoromethyl)-4-chlorophenyl)semicarbazide, 4,4-dimethyl-2-(3-(trifluoromethyl)-4-isopropoxyphenyl)semicarbazide and 4,4-dimethyl-2-(3-chloro-4-isopropoxyphenyl)semicarbazide are prepared.

Embodiment XI

4,4-Dimethyl-2-(2,4-dichlorophenyl)semicarbazide

To a solution of 21.35 g of 2,4-dichlorophenylhydrazine hydrochloride in 100 ml of pyridine was added dropwise at 0° C. with stirring 23.1 g of trifluoroacetic anhydride. After one hour at ambient temperature, the reaction mixture was poured into ice water and extracted with ether. The etheral layer was washed with cold 5% hydrochloric acid, dried and concentrated to dryness. Recrystallization from hexane gave 19.2 g (70%) of trifluoroacetic acid, 2-(2,4-dichlorophenyl)hydrazide as a white crystalline solid; melting point 127°–128° C.

A mixture containing 13.65 g of the above hydrazide and 29.7 g of phosgene in 300 ml of toluene was refluxed for 14 hours. The reaction mixture was concentrated to dryness. Recrystallization from hexane gave 8.25 g (55%) of 2-(trifluoromethyl)-4-(2,4-dichlorophenyl)-Δ$^2$-1,3,4-oxadiazolin-5-one as a white crystalline solid; melting point 44°–45° C.

To a solution containing 2.99 g of the above oxadiazolinone in 10 ml of tetrahydrofuran was added 1.1 g of dimethylamine. After standing for one hour at ambient temperature, the reaction mixture was diluted with 50 ml of ether, washed with dilute hydrochloric acid, then with water, dried and concentrated to dryness, to give 3.2 g (93%) of 4,4-dimethyl-1-(trifluoroacetyl)-2-(2,4-dichlorophenyl)semicarbazide, as a white crystalline solid; melting point 137°–138° C. (from ether-hexane), which is hydrolyzed to the desired product; an amber oil.

Embodiment XII

4,4-Diethyl-2-phenylsemicarbazide

A solution containing 19.8 g of 2-carbethoxyphenylhydrazine and 15 g of phosgene in 500 ml of xylene was heated at reflux for 8 hours (dry ice condenser) and then concentrated to a volume of about 250 ml. The reaction mixture was refluxed for 24 hours, and concentrated to dryness. The residual solid was recrystallized from ether-hexane (1:10) to give 21.5 g (95%) of 2-ethoxy-4-phenyl-Δ$^2$-1,3,4-oxadiazolin-5-one as a white crystalline solid; melting point 58°–60° C.

A solution of 12.0 g of the above oxadiazolinone and 9.4 g of diethylamine in 100 ml of ethyl acetate was refluxed for 4 hours. The reaction mixture was concentrated to dryness. The residual liquid, 16.4 g., was crystallized from ether to give 12.5 g (76%) of hydrazinecarboxylic acid, 2-(diethylcarbamoyl)-2-phenyl-, ethyl ester as a colorless crystalline solid; melting point 74°-76° C. Solid ethyl ester was hydrolyzed to the desired product, an oil in 78% yield.

Embodiments XIII-XXI

Following procedures similar to those in Embodiments XI and XII, the following compounds were prepared as shown in Table II which are readily hydrolyzable to the non-acylated semicarbazide as previously described.

TABLE II

2-Phenylsemicarbazides $$\underset{R^2}{\overset{R^1}{N}}-\underset{\|}{\overset{O}{C}}-N-\underset{H}{\overset{R^3}{N}}-\text{Ph-}X_m$$

| Embodiment | $R^1$ | $R^2$ | $R^3$ | $X_m$ | M.P., °C. | % Yield |
|---|---|---|---|---|---|---|
| XIII | $CH_3$ | $CH_3$ | $(CH_3)_3CC(O)-$ | 3-$CF_3$ | 144-5 | 85 |
| XIV | $C_2H_5$ | $C_2H_5$ | $C_2H_5OC(O)-$ | 3-Cl | 110-2 | 90 |
| XV | $CH_3$ | $CH_3$ | $C_2H_5OC(O)-$ | 3-Cl | 90-3 | 79 |
| XVI | $C_2H_5$ | $C_2H_5$ | $C_2H_5OC(O)-$ | 3,4-$Cl_2$ | 107-110 | 82 |
| XVII | $-CH_2(CH_2)_3CH_2-$ | | $C_2H_5OC(O)-$ | 3,4-$Cl_2$ | 125-7 | 56 |
| XVIII | $CH_3$ | $CH_3$ | $C_2H_5OC(O)-$ | 3-Cl,4-F | 69-73 | 69 |
| XIX | $CH_3$ | $CH_3$ | $C_6H_5OC(O)-$ | 3,4-$Cl_2$ | 101-4 | 99 |
| XX | $CH_3$ | $CH_3$ | $C_6H_5OC(O)-$ | 3-Cl,4-F | 114-8 | 75 |
| XXI | $CH_3$ | $CH_3$ | $CF_3C(O)-$ | 2,4-$Cl_2$ | 137-8 | 93 |

Embodiment XXII

4,4-Dimethyl-2-(3-chloro-4-isopropoxyphenyl)semicarbazide

A reactor was charged with 1,457.5 g of 3-chloro-4-isopropoxyphenylhydrazine hydrochloride and 5.5 l of toluene to which was slowly added 971.7 g of pyridine while stirring at 10°-15° C. The temperature was lowered to 5°-10° C. and 667.3 g of ethyl chloroformate was added over about 3 hours. The resulting mixture was stirred at 10°-20° C. for 2 hours, was washed with water and dried over MgSO4, and after filtration, evaporated to 4 liters. This solution was slowly added over about 3 hours to a stirred mixture of 3.7 l of toluene and 693 g of phosgene at 10°-15° C. The resulting mixture was stirred for about 3 hours at room temperature, then slowly heated to 85° C. to remove excess phosgene. The remaining mixture was cooled to 10° C. and 540 g of dimethylamine was added over about 3 hours while stirring and cooling to maintain a temperature of 10°-20° C. After stirring at room temperature for about 30 minutes, a solid product was filtered and washed with ether. The filtrate was evaporated to dryness, leaving a solid product. Washing the filter cake with water, left an oily residue which was triturated with ether to yield a white solid. To this solid combined with that obtained by evaporation of the filtrate was added 4.5 l of water, 960 g of 50% sodium hydroxide and 2.2 l of ethanol. The resulting mixture was heated at reflux for about 5 hours and then allowed to cool to room temperature. To this mixture 1.5 l of concentrated hydrochloric acid was slowly added while stirring. Carbon dioxide gas evolved. The resulting solution was then made basic by adding 500 ml of 50% sodium hydroxide while stirring. The resulting tan solid was filtered, air dried, triturated with hexane-ether (90:10) solution and, after filtration, dried to yield 957.3 g of solid product semicarbazide; melting point 73°-74° C.

Certain compounds disclosed herein are novel, 4,4-dimethyl-2-(4-chlorophenyl)semicarbazide and 4,4-dimethyl-2-(4-bromophenyl)semicarbazide, and have been found to be useful for controlling undesirable plant growth. That is, they have been found to be herbicidally effective against a wide range of plant species. The compounds exhibit a high degree of herbicidal activity in the control of a variety of economically important species of grasses and broadleaved weeds. The compounds are particularly useful as selective herbicides for use in certain important crops such as wheat.

The invention includes plant growth regulating (herbicidal) compositions comprising a carrier or a surface-active agent, or both a carrier and a surface-active agent, and, as active ingredient, at least one of the novel compounds. Likewise the invention also includes a method of controlling undesirable plant growth which comprises applying to the locus foliage or soil containing seeds an herbicidally effective amount of the novel compound.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing $\frac{1}{2}$–10% by weight of toxicant. Granules are usually prepared to have a size between 10 and 100 BS mesh (1.676–0.152 mm), and may be manufactured by agglomeration or impregnation techniques. Generally granules will contain $\frac{1}{2}$–25% by weight toxicant and 0–10% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the novel compounds of this invention comprises applying the compound ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

The preemergence herbicidal activity of the novel compounds was evaluated by planting seeds of watergrass, garden cress, downy brome, velvet leaf, yellow foxtail, wild mustard, cotton, grain sorghum, soybean and wheat in soil treated with test compounds at set dosages. The planted soil was held under controlled conditions of temperature, moisture, and light for 12 to 14 days. The amount of germination was then noted and the effectiveness of the test compound was rated visually on the basis of a 0 to 9 scale, 0 rating indicating no effect and 9 indicating death of the seedling or no germination. The compound of Embodiment III was found to be highly toxic to all species except for watergrass and wheat to which it was found to be moderately toxic. The compound of Embodiment IV was found to be highly toxic to garden cress, velvet leaf, yellow foxtail, wild mustard, cotton and wheat and moderately toxic to the remaining species.

The postemergence activity of the novel compounds was evaluated by spraying 7-day old crabgrass plants, 10-day old pigweed plants, 7-day old downy brome plants, 10-day old yellow foxtail, 10-day old wild mustard, 14-day old cotton plants, 10-day old grain sorghum plants and 7-day old wheat plants to runoff with a liquid formulation of test compound at set dosages. The sprayed plants were held under controlled conditions for 10 to 11 days and the effect of the test compound was then evaluated visually, the results being rated on the 0 to 9 scale discribed above. The compound of Embodiment III was highly toxic to pigweed, velvet leaf, wild mustard and soybeans, moderately toxic to downy brome and yellow foxtail and none to slightly toxic to crabgrass, cotton, grain sorghum and wheat. The compound of Embodiment IV was found to be highly toxic to pigweed, downy brome, velvet leaf, yellow foxtail, wild mustard, moderately toxic to crabgrass and soybean and none to slightly toxic to cotton, grain sorghum and wheat.

I claim:

1. A process for the preparation of a 2-phenylsemicarbazide which comprises the steps of
   (a) treating a phenylhydrazine, or salt thereof, with a chloroformate;
   (b) adding phosgene;
   (c) treating the resulting product with a secondary amine; and
   (d) hydrolyzing the resulting acylated semicarbazide product from (c) to a 2-phenylsemicarbazide.

2. A process according to claim 1 wherein the reactions of (a), (b) and (c) take place in the presence of a solvent.

3. A process according to claim 2 wherein the solvent is an ether or a hydrocarbon.

4. A process according to claim 1 wherein the reaction (a) takes place in the presence of a tertiary-amine.

5. A process according to claim 4 wherein the tertiary-amine is a lower alkyl tertiary amine in which each alkyl group contains from 1 to 6 carbon atoms.

6. A process according to claim 5 wherein the tertiary-amine is ethyl-diisopropylamine.

7. A process according to claim 1 wherein the secondary amine in step (c) is a dialkylamine in which each alkyl group contains from 1 to 6 carbon atoms.

8. A process according to claim 1 wherein the reaction mixture of step (b) is heated to reflux until the evolution of hydrogen chloride gas ceases.

9. A process according to claim 1 wherein the 2-phenylsemicarbazide product is 4,4-dimethyl-2-(3,4-dichlorophenyl)semicarbazide, 4,4-dimethyl-2-(3-chloro-4-fluorophenyl)semicarbazide, 4,4-dimethyl-2-(4-bromophenyl)semicarbazide, 4,4-dimethyl-2-(3-(trifluoromethyl)-4-chlorophenyl)semicarbazide, 4,4-dimethyl-2-(4-chlorophenyl)semicarbazide, 4,4-dimethyl-2-(3-(trifluoromethyl)-4-isopropoxyphenyl)semicarbazide or 4,4-dimethyl-2-(3-chloro-4-isopropoxyphenyl)semicarbazide.

10. A process for the preparation of a 2-phenylsemicarbazide which comprises treating a 4-phenyl-2-substituted-$\Delta^2$-1,3,4-oxadiazolin-5-one with a secondary amine $HNR^1R^2$ wherein $R^1$ and $R^2$ are hydrogen, alkyl or alkylene optionally interrupted by one or more oxygen atoms and hydrolyzing the resulting reaction product in the presence of an alkaline material to produce the desired 2-phenylsemicarbazide.

11. A process according to claim 10 wherein the reaction between the oxadiazolinone and amine is conducted in the presence of a solvent.

12. A process according to claim 10 wherein the secondary amine is a dialkylamine in which each alkyl group contains from 1 to 6 carbon atoms.

13. A process according to claim 10 wherein the oxadiazolinone starting material is a 4-(3,4-disubstituted-phenyl)-2-substituted-$\Delta^2$-1,3,4-oxadiazolin-5-one.

14. A process according to claim 10 wherein the hydrolysis is conducted using an alkali metal hydroxide.

15. A process according to claim 10 wherein the resulting 2-phenylsemicarbazide is 4,4-dimethyl-2-(3,4-dichlorophenyl)semicarbazide, 4,4-dimethyl-2-(3-chloro-4-fluorophenyl)semicarbazide, 4,4-dimethyl-2-(4-chlorophenyl)semicarbazide, 4,4-dimethyl-2-(3-trifluoromethyl)-4-chlorophenyl)semicarbazide, 4,4-dimethyl-2-(4-bromophenyl)semicarbazide, 4,4-dimethyl-2-(3-(trifluoromethyl)-4-isopropoxyphenyl)semicarbazide or 4,4-dimethyl-2-(3-chloro-4-isopropoxyphenyl)semicarbazide.

* * * * *